United States Patent [19]

Haber et al.

[11] Patent Number: 4,808,169
[45] Date of Patent: Feb. 28, 1989

[54] DISPOSABLE SAFETY SYRINGE HAVING MEANS FOR RETRACTING ITS NEEDLE CANNULA INTO ITS MEDICATION CARTRIDGE

[75] Inventors: Terry M. Haber, Lake Forest; Clark B. Foster, El Toro; William H. Smedley, Lake Elsinore, all of Calif.

[73] Assignee: Habley Medical Technology Corporation, Laguna Hills, Calif.

[21] Appl. No.: 176,305

[22] Filed: Mar. 31, 1988

Related U.S. Application Data

[63] Continuation-in-part of Ser. No. 143,751, Jan. 14, 1988.

[51] Int. Cl.⁴ ............................................. A61M 5/32
[52] U.S. Cl. ..................................... 604/195; 604/196; 604/110
[58] Field of Search ............... 604/195, 196, 198, 110, 604/263, 232

[56] References Cited

U.S. PATENT DOCUMENTS 4,507,117  3/1985  Vining et al. ................... 604/196
4,692,156  9/1987  Haller ............................. 604/195

Primary Examiner—John D. Yasko
Attorney, Agent, or Firm—Morland C. Fischer

[57] ABSTRACT

A disposable safety syringe, such as a dental syringe, comprising a syringe cylinder having proximal and distal ends, a pre-filled fluid medication cartridge movable through the cylinder, and a double-ended hypodermic needle cannula extending through and being retained at the distal end of the cylinder between a pair of rotatable jaws. A piston is movable distally through the cartridge for expulsing the fluid contents via the needle cannula and for engaging one end of the cannula. The cartridge is moved through the cylinder and into contact with the needle retaining jaws to cause said jaws to be rotated relative to the needle cannula. Accordingly, the jaws are moved out of engagement with the needle cannula. The piston is then moved proximally through the medication cartridge for correspondingly retracting the needle cannula past the jaws and into the empty medication cartridge, wherein the cannula is completely shielded and irretrievably located. The syringe is now rendered non-reuseable and suitable for a safe disposal without subjecting health care workers to an accidental needle strike as a consequence of a careless handling or cutting of the cannula.

16 Claims, 5 Drawing Sheets

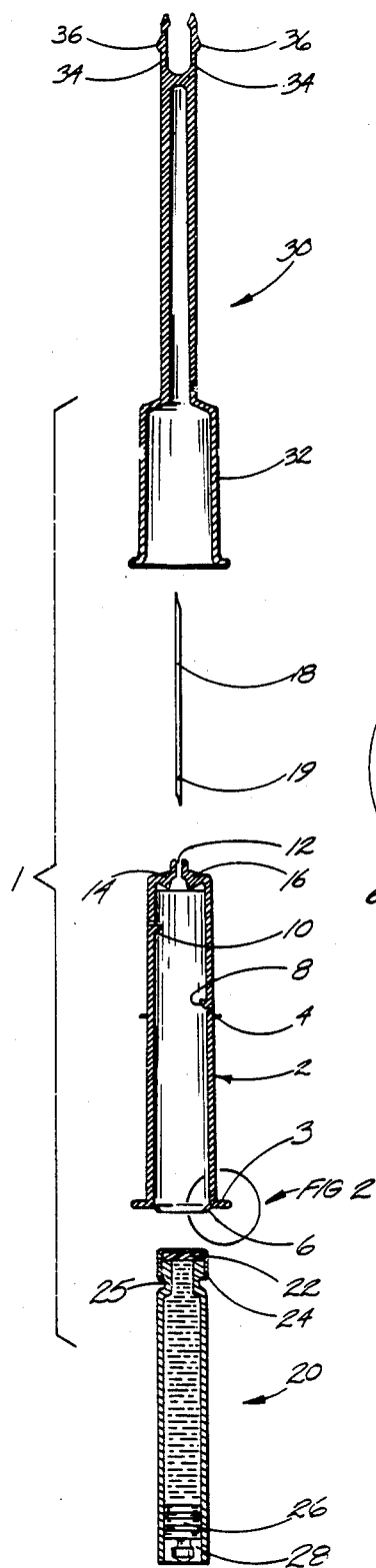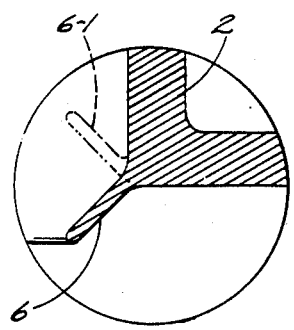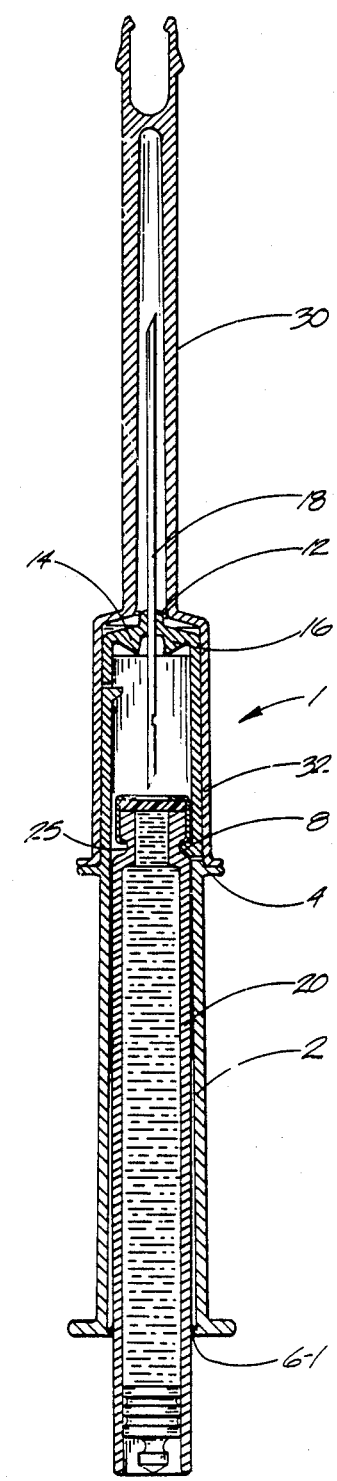
fig 1
fig 2
fig 3

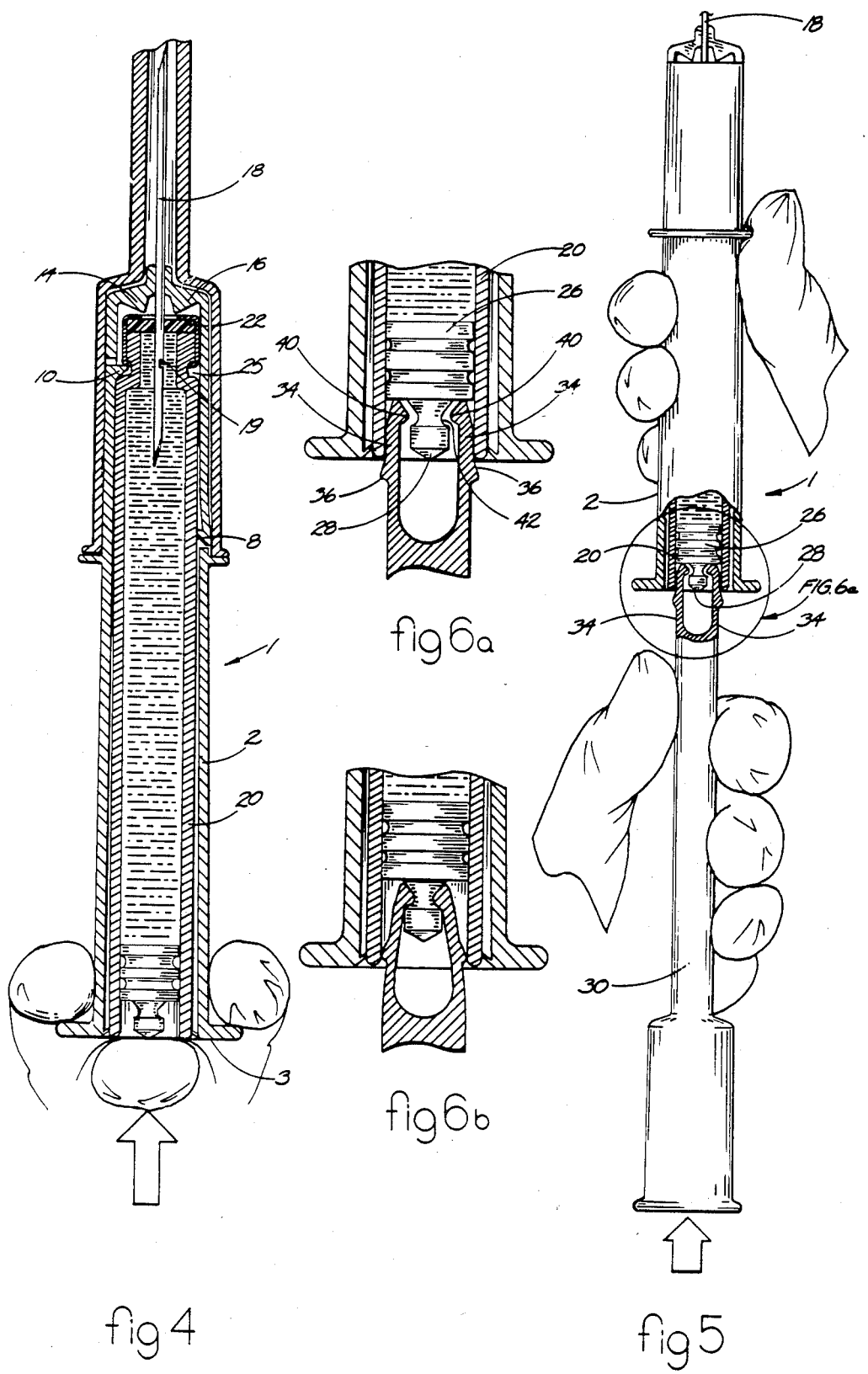

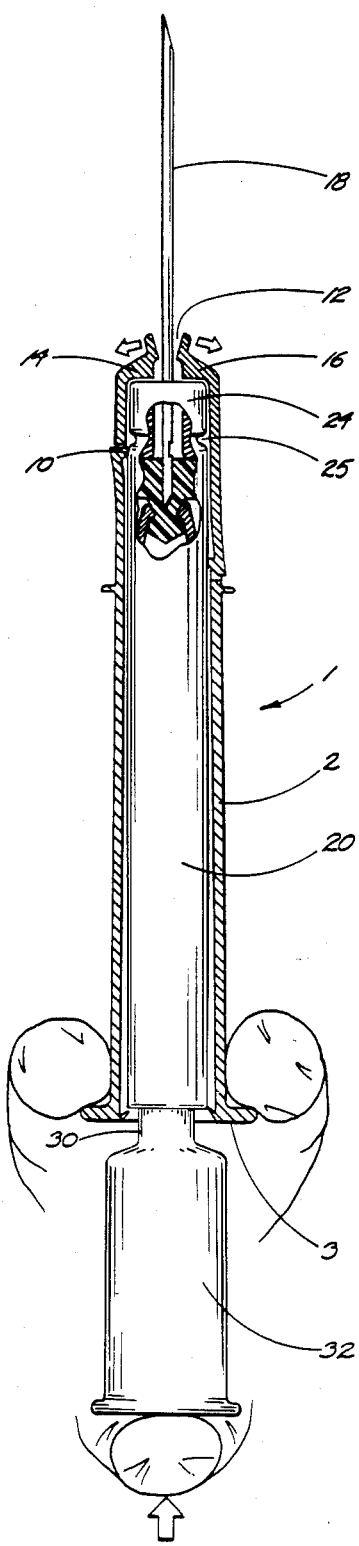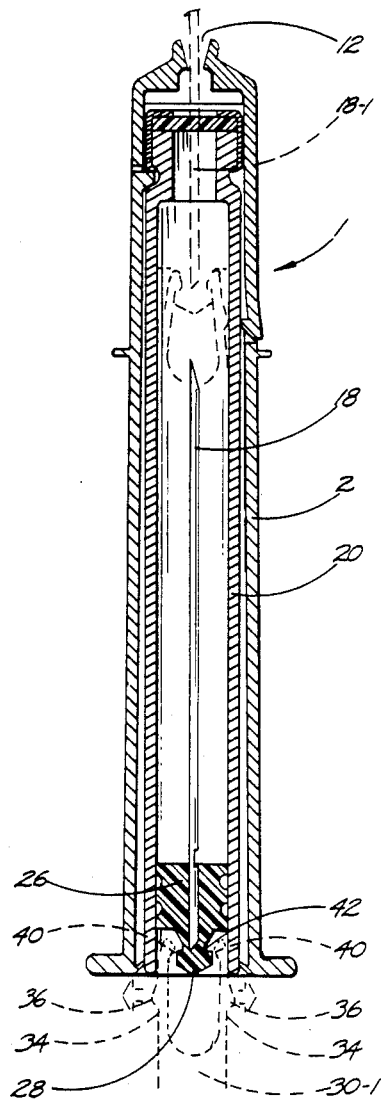
fig 7
fig 8

DISPOSABLE SAFETY SYRINGE HAVING MEANS FOR RETRACTING ITS NEEDLE CANNULA INTO ITS MEDICATION CARTRIDGE

CROSS-REFERENCES TO RELATED APPLICATIONS

This application is a continuation-in-part of Application Ser. No. 143,751 filed Jan. 14, 1988, pending.

BACKGROUND OF THE INVENTION

1. Field of the Invention

This invention relates to a disposable safety syringe, such as a dental syringe, having a pre-filled fluid medication cartridge and a double-ended hypodermic needle cannula, and, more particularly, to means by which the needle cannula may be relocated from an axially extended position, at which to inject the fluid contents of the medication cartridge into a targeted tissue area, to a retracted position, at which the cannula is withdrawn into and completely shielded by the medication cartridge at the interior of the syringe cylinder.

2. Prior Art

Dental syringes of the type having a pre-filled cartridge of fluid medication and a double-ended hypodermic needle are well-known in the art for injecting such medication from the cartridge to a targeted tissue area of a patient. However, at the completion of the injection, the needle is typically locked in an axially extended position projecting outwardly from a distal bore formed through the syringe cylinder.

In some cases, the syringe may be used to treat a patient having a communicable disease. Prior to disposing the syringe, the hypodermic needle is frequently broken or destroyed to prevent reuse. Dental office workers are especially susceptable to accidental and potentially infectious needle strikes due to the careless handling or breaking of the needle and disposing of the syringe after use. The resulting mini-accident caused by an accidental needle strike typically requires a blood test for such diseases as AIDS and hepatitis. The corresponding cost and inefficiency of testing dental office workers who have received such an accidental needle strike result in considerable waste, which may be particularly damaging to a dental facility which is striving for economy.

The following patent applications, which are assigned or will be assigned to the assignee of the present patent application, diclose syringes having a pre-filled medication cartridge and a needle which is retractable within the syringe cylinder:

Application Ser. No. 39,715 filed Apr. 20, 1987 and entitled "DENTAL SYRINGE HAVING AN AUTOMATICALLY RETRACTABLE NEEDLE", Application Ser. No. 101,251 filed Sept. 25, 1987 and entitled "DISPOSABLE, PRESTERILIZABLE SYRINGE FOR A PRE-FILLED MEDICATION CARTRIDGE", and Application Ser. No. 143,751 entitled "RETRACTABLE NEEDLE SYRINGE WITH INTEGRAL SPRING".

SUMMARY OF THE INVENTION

Briefly, the present invention relates to a disposable safety syringe, such as a dental syringe, or the like, by which a hypodermic needle cannula may be retracted into an evacuated medication cartridge at the interior of the syringe cylinder so as to prevent reuse of the syringe and permit the syringe to be safely handled and discarded without subjecting health care workers to an accidental needle strike and the spread of a contagious and, possible life threatening, disease. According to a first embodiment of the invention, the syringe includes a hollow cylinder having proximal and distal ends and a bore formed through the distal end. A pair of inwardly projecting needle retaining shoulders are hingedly connected to the distal end of the cylinder to define a bore therebetween. A double-ended needle cannula extends through and is retained within the distal bore by means of a thermal bond to prevent movement of the cannula relative to the bore. A first end of the cannula extends into the interior of the cylinder, and an opposite, second end of the cannula extends outwardly from the cylinder for administering an injection at a targeted tissue area.

A pre-filled fluid medication cartridge is loaded into the cylinder through the proximal end so as to be spaced axially from the first end of the needle cannula. The cartridge contains a piston which is movable through the cartridge to expulse the fluid contents. A combination needle sheath/piston stem has a relatively wide sleeve formed at one end and a pair of flexible gripping arms projecting axially from the opposite end. Initially, the wide sleeve of the needle sheath/piston stem surrounds and sheaths the second end of the needle cannula to prevent the contamination thereof and avoid an accidental needle strike.

In operation, the medication cartridge is advanced distally through the syringe cylinder until the first end of the needle cannula penetrates the cartridge to communicate with the fluid contents thereof. The second end of the cannula is unsheathed, and the flexible gripping arms of the needle sheath/piston stem are detachably connected to the piston at the interior of the medication cartridge to complete a piston assembly. An axial force is then applied to the piston stem to correspondingly drive the piston distally through the cartridge to expulse the contents thereof via the cannula, such that the piston is penetrated by the first end of the cannula. After the medication cartridge has been emptied, the axial force is reapplied to the piston stem to cause the cartridge to move distally through the syringe cylinder and into contact with the needle retaining shoulders at the distal end of the cylinder. The axial force is transferred from the cartridge to the distal end of the cylinder, whereby to cause the needle retaining shoulders to rotate relative to the needle cannula and thereby break the bond formed between the shoulders and the cannula. The distal bore is thereby opened to release the cannula therefrom. The piston stem then moves the piston proximally through the cartridge to correspondingly retract the cannula through the opened distal bore and into the medication cartridge, wherein the cannula is completely shielded and irretrievably located.

According to a second embodiment of the invention, a medication cartridge is loaded into a syringe cylinder having open proximal and distal ends. A double-ended needle cannula is releasably retained at the distal end of the cylinder in fluid communication with the cartridge by and between a pair of rotatable jaws. Each jaw has a respective contact face by which to engage the cannula and an adjacent beveled surface having a channel formed therein.

The medication cartridge is emptied via the needle cannula in the same manner described while referring to the syringe of the first embodiment. An axial force is then applied to the piston stem to drive the empty cartridge distally through the syringe cylinder and into contact with the needle retaining jaws at the distal end of the cylinder. The axially applied force is transferred from the cartridge to the jaws, whereby to cause said jaws to rotate relative to the needle cannula. Accordingly, the respective contact faces of the jaws are moved out of engagement with the needle cannula. The adjacent beveled surfaces of the jaws are thereby rotated into face-to-face alignment with one another so that the cannula is received and floating freely within the respective channels of the beveled surfaces. The piston stem then moves the piston proximally through the empty cartridge to retract the cannula through the channels of the jaws and into the medication cartridge, wherein the cartridge is completely shielded and irretrievably located.

BRIEF DESCRIPTION OF THE DRAWINGS

FIG. 1 is an exploded view of the disposable safety syringe which forms the present invention;

FIG. 2 is an enlarged detail of the syringe of FIG. 1;

FIG. 3 is a cross-section showing the syringe of FIG. 1 in the assembled relationship;

FIG. 4 illustrates the operational step of moving a medication cartridge distally through the syringe cylinder until a needle cannula penetrates the cartridge at the interior of the syringe cylinder;

FIG. 5 illustrates the detachable connection of a piston stem to a piston of the medication cartridge by which the piston can be moved axially through the cartridge;

FIGS. 6a and 6b illustrate enlarged details for detachably connecting the piston stem to the piston of FIG. 5;

FIG. 7 illustrates the operational step of moving the medication cartridge distally through the syringe cylinder and into contact with the distal end of the cylinder for breaking the bond formed between the needle cannula and a distal bore;

FIG. 8 illustrates the operational step of moving the piston proximally through the medication cartridge for retracting the needle cannula through the distal bore and into said cartridge;

DESCRIPTION OF THE PREFERRED EMBODIMENTS

Figure 9:
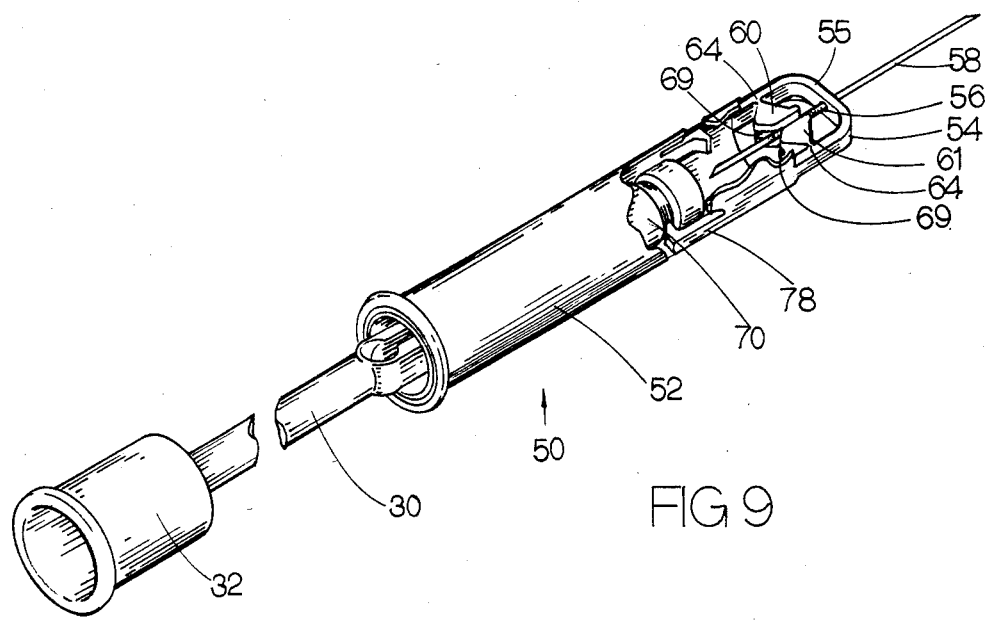
FIG. 9 is an isometric view of a disposable safety syringe which forms a second embodiment of the present invention.

The disposable safety syringe 1 of the present invention is best described while referring to the drawings, where FIG. 1 illustrates an exploded view of the syringe components. More particularly, syringe 1 includes a hollow cylinder or barrel 2 having an open proximal end and a partially closed distal end. A major flange 3 extends around the open proximal end of the syringe cylinder 2. A relatively narrow flange 4 extends around the periphery of cylinder 2 intermediate the proximal and distal ends. An integral, flexible sealing gasket 6 projects outwardly through the open proximal end of cylinder 2. The details of gasket 6 will be described in greater detail hereinafter when referring to FIG. 2. Proximal and distal locking detents 8 and 10 project inwardly from opposite sides of the cylinder 2. The functions performed by locking detents 8 and 10 will be better described when referring to FIG. 3. Briefly, however, a notch (best illustrated in FIG. 3) is formed through cylinder 2 around the top and sides of locking detents 8 and 10 to permit detents 8 and 10 to rotate slightly in an outward direction relative to cylinder 2.

The distal end of cylinder 2 includes a narrow bore 12 which receives and retains a double-ended hypodermic needle cannula 18 to permit fluid to be delivered from the syringe 1 to a targeted tissue area of a patient. Needle cannula 18 includes a fluid port 19 (best shown in FIG. 3) which enables substantially all of the fluid from syringe 1 to be injected into the targeted tissue area. The distal bore 12 is defined by a pair of oppositely disposed needle retaining shoulders 14 and 16 which, as will soon be explained, are hingedly connected to the distal end of cylidner 2 so as to be adapted for rotation in an outward direction relative to the cylinder (best illustrated in FIG. 7).

A pre-filled medication cartridge or ampule 20 is of suitable size so as to be loaded into the syringe cylinder 2 through the open proximal end thereof so that the contents of cartridge 20 may be delivered to the targeted tissue area via needle cannula 18. Cartridge 20 is typically formed from a transparent material (e.g. glass, or the like) and is filled with a fluid medication, such as Novacaine, or the like. A rubber seal 22 extends across a distal end of cartridge 20, and a metal end cap 24 secures seal 22 to the cartridge. A neck 25 of relatively reduced diameter is formed around the periphery of cartridge 20 below end cap 24. A piston 26 is located at the proximal end of cartridge 20. Piston 26 is slideable axially through the cartridge to expulse the fluid contents thereof (via cannula 18). The piston 28 of cartridge 26 includes a proximally projecting plug member 28, the purpose and advantage of which will be described when referring to FIGS. 6a and 6b.

Syringe 1 also includes a combination needle sheath and piston stem 30. The combination needle sheath and piston stem 30 has a substantially hollow, elongated body with a relatively wide sleeve 32 formed at one end and a pair of oppositely disposed, flexible gripping arms 34 projecting from the opposite end. A small locating bump 36 projects outwardly from each gripping arm 34. As is best shown in FIG. 3, the combination needle sheath/piston stem 30 functions as a needle sheath, such that sleeve 32 receives and surrounds one end of the needle cannula 18. As is best shown in FIG. 5, needle sheath/piston stem 30 also functions as a piston stem, such that the pair of gripping arms 34 are releasably connected to the piston 26 of medication cartridge 20 to form a piston assembly.

FIG. 2 show an enlarged detail of the flexible sealing gasket 6 which is integrally connected to the proximal end of syringe cylinder 2. More particularly, gasket 6 is hingedly connected to cylinder 2 so as to be adapted for rotation from an outwardly projecting position (as illustrated in FIG. 1) to an inwardly projecting position relative to the interior of cylinder 2 (as shown in phantom and designated by the reference numeral 6-1 of FIG. 2). The means and advantage for rotating sealng gasket 6 into the interior of cylinder 2 is now described while referring to FIG. 3.

FIG. 3 shows the disposable safety syringe 1 in an assembled configuration so as to be suitable for packaging and shipment to health care workers. In the assembled relationship, the needle cannula 18 is retained within the distal bore 12 of syringe cylinder 2 by a thermal bond that is formed between the cannula and the opposing needle retaining shoulders 14 and 16. One end of cannula 18 extends proximally into the interior of cylinder 2 and is adapted to penetrate the seal of the medication cartridge 20. The opposite end of cannula 18 extends distally and outwardly from the cylinder 2 for injecting the contents of cartridge 20 into the targeted tissue area. The distally extending end of needle cannula 18 is initially surrounded and protected by the needle sheath 30 so as to preserve the sterility of cannula 18 and prevent an accidental needle strike. More particularly, the relatively wide sleeve 32 of needle sheath 30 is placed over the proximal end of cylinder 2 until a flanged end of sheath 30 engages the intermediate flange 4 of cylinder 2. It may be desirable to heat seal sleeve 32 to flange 4 to prevent a premature removal of needle sheath 30 from cylinder 2.

The medication cartridge 20 is loaded through the open proximal end of and advanced distally through the syringe cylinder 2 until the proximal locking detent 8 is received in a snap-fit engagement within the neck 25 of cartridge 20. Accordingly, cartridge 20 is initially retained within cylinder 2 in spaced, axial alignment with the needle cannula 18, such that a small portion of the cartridge 20 extends outwardly from the proximal end of cylinder 2.

At the same time that medication cartridge 20 is loaded into the syringe cylinder 2, the flexible sealing gasket 6 is engaged by cartridge 20 and rotated from the outwardly projecting position of FIG. 1 to the inwardly projecting position (represented by reference numeral 6-1) of FIG. 2. That is, the distal advancement of cartridge 20 through cylinder 2 automatically rotates gasket 6, so that an air-tight seal is formed between cylinder 2 and cartridge 20 to preserve the sterility of needle 18 by preventing contaminated air from reaching cannula 18 via the space between the cylinder 2 and the cartridge 20.

The operation of the syringe 1 of the present invention is now described while referring to FIGS. 4-8 of the drawings. In FIG. 4, the user places his index and middle fingers under the major flange 3 of syringe cylinder 2 and his thumb against the end of medication cartridge 20 which extends outwardly from the cylinder 2 (best represented in FIG. 2). The user then uses his thumb to exert an axial force upon the medication cartridge 20 (in the direction of the reference arrow) by which to rotate proximal locking detent 8 out of engagement with the neck 25 of cartridge 20 and thereby permit cartridge 20 to be driven distally through cylinder 2. The continued application of the axial force to cartridge 20 causes the cartridge to slide through cylinder 2 until the respective proximal ends of cartridge 20 and cylinder 2 lie adjacent one another and the proximally extending end of cannula 18 penetrates the rubber seal 22 to communicate with the fluid contents of cartridge 20, so that an injection of the contents may be subsequently administered. Accordingly, the distal locking detent 10 is received in a snap-fit engagement within the neck 25 of cartridge 20, and the cartridge 20 is retained in spaced proximity to the needle retaining shoulders 14 and 16 at the distal end of syringe cylinder 2.

In FIG. 5 of the drawings, the user removes the needle sheath/piston stem 30 to unsheath the distally extending end of needle cannula 18. The user then grasps the cylinder 2 of syringe 1 with one hand and uses his opposite hand to attach needle sheath/piston stem 30 to the piston 26 of medication cartridge 20 to complete a piston assembly comprising a piston head 26 and an elongated piston stem 30.

More particularly, and referring concurrently to FIGS. 5 and 6 of the drawings, the user applies an axial force (in the direction of the references arrow in FIG. 5) to the piston stem 30 to move the flexible gripping arms 34 through the proximal end of medication cartridge 20 and adjacent the plug member 28 of piston 26. As is best shown in FIG. 6a, each gripping arm 34 terminates at an inwardly projecting retaining finger 40. As the piston stem 30 is moved through the cartridge 20 (in the manner illustrated in FIG. 6b) to drive the piston 26 distally through the cartridge, the locating bumps 36 of gripping arms 34 will contact the interior walls of cartridge 20, whereby to cause the flexible gripping arms 34 to rotate inwardly towards plug member 28. A rotation of the gripping arms 34 correspondingly causes the inwardly projecting retaining fingers 40 to be rotated into engagement with and releasably retained by a relatively narrow neck 42 formed around the plug member 28 of piston 26. Therefore, so long as the locating bumps 36 on gripping arms 34 of piston stem 30 are located within the interior of medication cartridge 20, the retaining fingers 40 will be held within the neck 42 of plug member 28 to prevent the detachment of piston stem 30 from piston 26.

In FIG. 7 of the drawings, the user administers an injection by keeping his index and middle fingers located behind the major flange 3 of cylinder 2 and relocating his thumb to the sleeve 32 of piston stem 30. The user then applies an axial force to sleeve 32 (in the direction of the reference arrow) to drive the piston 26 distally through medication cartridge 20 to expulse the fluid contents thereof through the needle cannula 18 and into the targeted tissue area of the patient. It may be noted that by virtue of the fluid port 19 in cannula 18, substantially all of the fluid may be expulsed from cartridge 20 as the piston 26 is advanced to the distal end of the cartridge. Moreover, the proximally extending end of the needle cannula 18 penetrates and is thereby connected to piston 26 when the piston is moved completely through cartridge 20 to expulse the fluid therefrom.

Once the medication cartridge 20 has been emptied and the injection completed, the user continues to apply an axial force to the sleeve 32 of piston stem 30. Accordingly, the piston 26 (which has already been driven to the distal end of cartridge 20) transfers the axially applied force to the cartridge, so as to cause the distal locking detent 8 to rotate out of engagement with the neck 25 of cartridge 20 and thereby permit an additional distal movement of the cartridge through the syringe cylinder 2. The continued application of the axially applied force to sleeve 32 advances medication cartridge 20 distally through cylinder 2 until the metal end cap 24 thereof is moved into contact with needle retaining shoulders 14 and 16. The axially applied force is then transferred from the cartridge 20 to the inwardly projecting needle retaining shoulders 14 and 16 to cause said shoulders to rotate (in the direction of the reference arrows) around their respective integral (i.e. living) hinges at the distal end of cylinder 2 to thereby break the thermal bond between needle cannula 18 and shoulders 14 and 16. With the bond broken and the needle 18 no longer retained between shoulders 14 and 16, the needle cannula 18 is free to move relative to shoulders 14 and 16 through the distal bore 12 of syringe cylinder 2.

To this end, FIG. 8 of the drawings shows the needle cannula 18 of syringe 1 being withdrawn through the distal bore 12 to be retracted within and completely surrounded by the empty medication cartridge 20. More particularly, the user grasps and pulls the piston stem 30 proximally through cylinder 2, whereby the needle is relocated from an axially extended position (shown in phantom and designated by reference numeral 18-1) to an inwardly retracted position. When the piston stem (shown in phantom and designated 30-1) is pulled to the proximal end of medication cartridge 20, such that the locating bumps 36 are removed therefrom, the retaining fingers 40 of the respective gripping arms 34 are automatically rotated (in the direction of the reference arrows) out of engagement with the neck 42 of piston plug member 28. Therefore, the piston stem 30 may be detached from piston 26 and discarded. However, the piston 26 remains disposed within the proximal end of cartridge 20, such that the needle 18 is retained at an inaccessible location within the interior of the cartridge. Accordingly, the syringe 1 is now suitable for disposal with the needle cannula 18 safely retracted within and completely shielded by both the medication cartridge 20 and the cylinder 2, whereby to prevent a reuse of the syringe 1 and its cannula 18 and avoid an accidental needle strike and the spread of a communicable and, possibly life threatening, disease by eliminating the need to handle or cut the cannula as has heretofore been required with conventional syringes.

A modification of the disposable safety syringe of FIGS. 1-8 is shown in FIGS. 9-14 of the drawings. As was previously indicated when referring to FIG. 3 of the drawings, a double-ended needle cannula is firmly bonded to the distal bore of a syringe cylinder between a pair of needle retaining shoulders. In the modification of FIGS. 9-14, a double-ended needle cannula is frictionally engaged and releasably retained at the distal end of a syringe cylinder by means of a pair of movable needle retaining jaws.

Figures 10, 11:
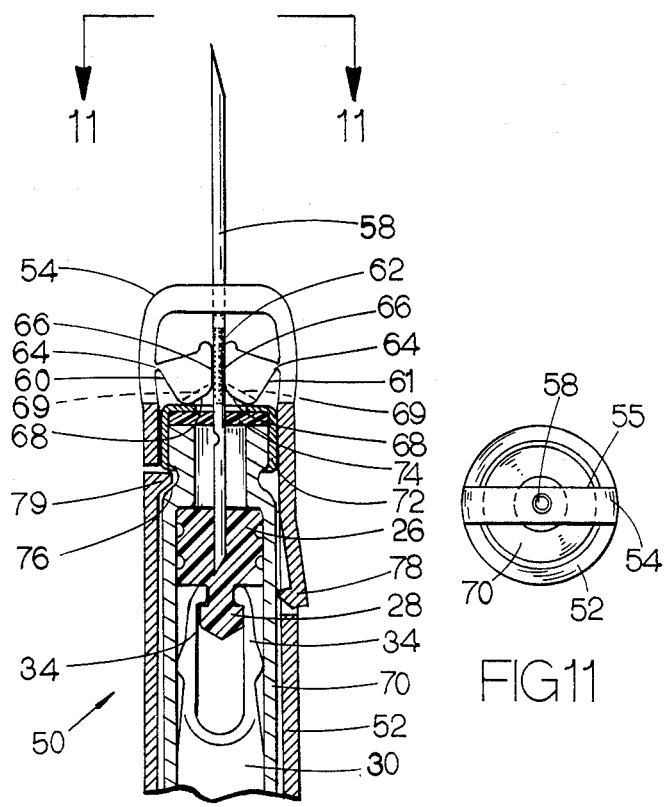
FIG. 10 shows the syringe of FIG. 9 with a needle cannula being engaged by and releasably retained between a pair of rotatable jaws.
FIG. 11 is an end view taken along lines 11—11 of FIG. 10.

More particularly, and referring initially to FIGS. 9-11, a disposable safety syringe (such as a dental syringe) 50 is shown including a hollow cylinder 52 having open proximal and distal ends. Extending upwardly from and then access the open distal end of syringe cylinder 52 is a needle supporting bridge 54 that is preferably formed from a resilient material. Bridge 54 has an aperture 56 formed through a cross member 55 thereof by which to receive and support a double ended hypodermic needle cannular 58 in coaxial alignment with the cylinder 52.

The needle cannula 58 is engaged and retained at the distal end of the cylinder 52 by a pair of oppositely disposed needle retaining jaws 60 and 61. Needle retaining jaws 60 and 61 project radially inward and towards one another from respective sides of the needle supporting bridge 54. Retaining jaws 60 and 61 are narrowly spaced from one another along the longitudinal axis of the syringe cylinder 52. Therefore, a needle cannula 58 can be located in the narrow space between the opposing retaining jaws 60 and 61 and retained therein by means of friction so as to prevent the inadvertent detachment of and/or axial relocation of cannula 58 relative to jaws 60 and 61. To this end, the cannula 58 may be provided with an irregularly textured surface 62 (best shown in FIG. 10), whereby to enhance the frictional engagement of cannula 58 by retaining jaws 60 and 61.

Each needle retaining jaw 60 and 61 is connected to a respective side of needle supporting bridge 54 by an integral hinge 64. As will soon be explained, the application of an axial and distally directed force to needle retaining jaws 60 and 61 to cause said jaws to rotate around hinges 64 for movement out of engagement with needle cannula 58. Each retaining jaw 60 and 61 also includes a flat contact face 66. In the configuration of FIGS. 9-11, the contact faces 66 of jaws 60 and 61 are arranged in spaced, parallel alignment with one another for retaining the needle cannula 58 therebetween by means of the aforementioned frictional engagement thereof.

A surface portion 68 of each needle retaining jaw 60 and 61 below the flat contact face 66 is beveled. Such beveled surfaces 68 permit the retaining jaws 60 and 61 to rotate around their respective hinges 64 in response to a distally directed force (as will soon be described). That is to say, without the presence of beveled surfaces 68, the retaining jaws 60 and 61 would be unable to rotate, as a consequence of their proximity to the longitudinally extending needle cannula 58. To this end, and as will be described in greater detail when referring hereinafter to FIGS. 12 and 13, a longitudinal channel 69 is formed in each beveled surface 68 so as to receive the cannula 58 during the rotation or retaining jaws 60 and 61.

Similar to the syringe of FIGS. 1-8, a pre-filled medication cartridge or ampule 70 is loaded into the syringe cylinder 62 through the open proximal end thereof, so that the contents of the cartridge 70 may be injected into a targeted tissue area of a patient via needle cannula 58. Cartridge 70 includes a metal end cap 72 which secures a rubber seal 74 across the distal end of the cartridge. A neck 76 of relatively reduced diameter is formed around the periphery of the cartridge 70 below end cap 72. A piston 26 is located at the proximal end of cartridge 70 and is slideable axially therethrough to expulse the contents of the cartridge via cannula 58. Piston 26 includes an integrally formed, proximally projecting plug member 28. Inasmuch as the piston 26 and plug member 28 of the syringe 50 of FIGS. 9-14 are identical to the piston and plug member of the syringe of FIGS. 1-8, identical reference numerals will be used and no further description of said piston 26 and plug member 28 will be provided.

Syringe 50 also includes a combination needle sheath and piston stem 30. The needle sheath/piston stem 30 has an elongated body with a wide and hollow sleeve 32 formed at one end and a pair of flexible gripping arms 34 projecting from the opposite end. Inasmuch as the combination needle sheath/piston stem 30 of the syringe 50 of FIGS. 9-14 is identical to the needle sheath/piston stem of the syringe of FIGS. 1-8, identical reference numerals will be used, and no further description of said needle sheath/piston stem 30 will be provided, except to say that the needle sheath/piston stem functions as a needle sheath when the sleeve 32 thereof surrounds one end of the cannula 58, or, as a piston stem, when the pair of gripping arms 34 are releasably connected to the plug member 28 of piston 26 to form a complete piston assembly (as is illustrated in FIGS. 9 and 10).

The operation of the syringe 50 is now described while referring to FIGS. 9-14 of the drawings. FIG. 9 illustrates the syringe 50 in the pre-injection mode (similar to the syringe illustrated in FIG. 3) with medication cartridge 70 spaced axially from the needle cannula 58. The cartridge 70 is retained at the axially spaced position relative to cannula 58 when a proximal locking detent 78 of syringe cylinder 52 is detachably received within the narrow neck of the cartridge.

FIG. 10 shows the syringe 50 in the injection mode (similar to the syringe illustrated in FIG. 5) after medication cartridge 70 has been detached from the proximal locking detent 78 and moved axially through syringe cylinder 52 and the piston plug member 26 has been engaged by piston stem 30 and moved distally through the cartridge, so that the needle cannula 58 penetrates the rubber seal 74 of cartridge 70 and the contents of said cartridge are expulsed via cannula 58 for the purpose of administering an injection. The cartridge 70 is retained in communication with needle cannula 58 when a distal locking detent 79 of cylinder 52 is detachably received within the narrow neck 76 of the cartridge.

Figure 12:
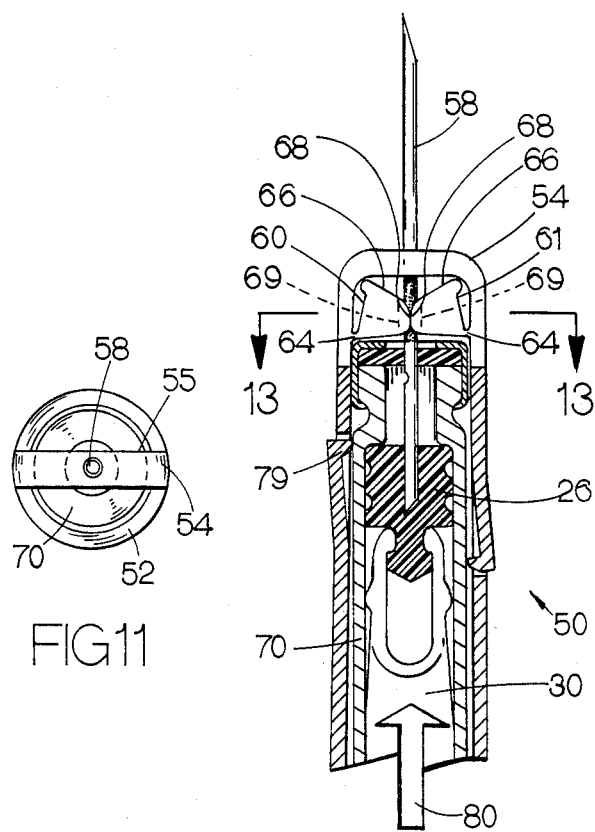
FIG. 12 shows the syringe of FIG. 9 with the rotatable jaws rotated out of engagement of the needle cannula.

Once the medication cartridge 70 of syringe 50 has been emptied and the injection completed, the health care worker applies an axial force to the piston stem 30 (in the direction of the reference arrow 80 of FIG. 12). Accordingly, and referring now to FIGS. 12 and 13 of the drawings, the axial force is transferred from piston stem 30 to the empty medication cartridge 70 via piston plug member 26, whereby to move cartridge 70 out of engagement by the distal locking detent 79 and into contact with the needle retaining jaws 60 and 61. The axially applied force is then transferred from the cartridge 70 to retaining jaws 60 and 61 to cause said jaws to rotate at the respective integral hinges 64 in a direction away from needle cannula 58. By virtue of its resilient nature, the sides of needle supporting bridge 54 are permitted to bow outwardly to accommodate the rotation of jaws 60 and 61 against cannula 58. Accordingly, the needle cannula 58 will be released from its former frictional engagement by and between the opposing flat contact faces 66 of needle retaining jaws 60 and 61.

Figure 13:
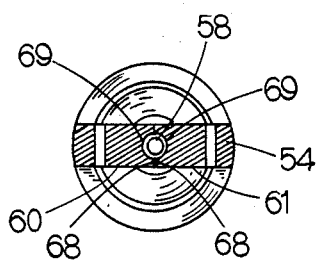
FIG. 13 is a cross-section taken along lines 13—13 of FIG. 12.

The retaining jaws 60 and 61 will continue to rotate in response to an axial force applied thereto by the distally advancing medication cartridge 70 until the beveled surfaces 68 thereof are arranged in face-to-face alignment with one another. As is best shown in FIG. 13, the needle cannula 58 is received within the respective longitudinal channels 69 which are formed in the opposing beveled surfaces 68. Therefore, the cannula 58, which is now retained at only one end thereof (i.e. from the piston 26) floats freely within the adjacent channels 69 of the beveled surfaces 68 and the aperture 56 formed in the cross member of the needle supporting bridge 54.

Figure 14:
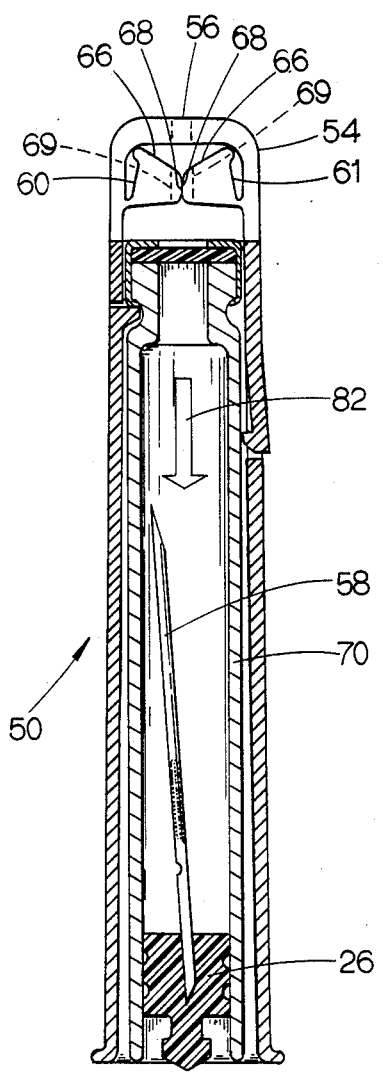
FIG. 14 shows the syringe of FIG. 9 with the needle cannula removed from the jaws and retracted into a medication cartridge located within the cylinder of the syringe.

Referring now to FIG. 14, the freely floating needle cannula 58 of syringe 50 is withdrawn (in the direction of the reference arrow 82) through the aperture 56 in bridge 54 and the adjacent channels 69 of needle retaining jaws 60 and 61 so as to be retracted within and completely surrounded by the empty medication cartridge 70. Inasmuch as the procedure for withdrawing the cannula 58 into the cartridge 70 of syringe 50 is identical to the procedure disclosed when referring to the syringe of FIG. 8, no further description of this procedure will be provided, except to say that the health care worker pulls the piston stem (designated 30 in FIG. 12) proximally through medication cartridge 70, whereby the cannula 58, which is attached to the piston 26, is relocated from an axially extended position (as illustrated in the injection mode of FIG. 10) to a retracted position (as illustrated in the needle retraction mode of FIG. 14).

Because of non-uniform deformation stresses within the piston and axial deflections produced by needle retaining jaws 60 and 61, the needle cannula 58 is retracted into the cartridge 70 in a canted alignment relative to the longitudinal axis of the cylinder 52. Therefore, the needle cannula 58 will be blocked (e.g. by the end cap of the cartridge) during any attempt to return the cannula axially and distally through the cartridge to the axially extended position of FIG. 10.

As was also previously described when referring to FIG. 8, the piston stem may now be detached from piston 26 and discarded. However, the piston 26 remains at a proximal position within medication cartridge 70, such that the cannula 58 is inaccessably located at the interior of the cartridge. Hence, the syringe 50 is now suitable for disposal with the needle cannula safely retracted within and completely shielded by both the medication cartridge 70 and the syringe cylinder 52, whereby to prevent a reuse of the syringe and its cannula and thereby avoid an accidental needle strike and the spread of a contagious, and possibly life threatening, disease.

It will be apparent that while a preferred embodiment has been shown and described, various modifications and changes may be made without departing from the true spirit and scope of the invention. For example, the syringes 1 and 50 of the present invention has been described as having application as a dental syringe. Nevertheless, this should not be regarded as a limitation of the scope of the invention, and the claims which are appended hereto are applicable to other syringes, especially those which use a pre-filled medication cartridge, where it is desirable to retract the needle cannula within the cartridge in order to render the syringe safe for handling and/or disposal.

Having thus set forth a preferred embodiment of the invention, what is claimed is:

1. A syringe comprising:
   a hollow cylinder having proximal and distal ends;
   a cartridge located within said cylinder and containing a supply of fluid;
   a needle cannula extending outwardly from the distal end of said cylinder and projecting into said cylinder to communicate with said cartridge so that said fluid supply may be injected from said cartridge via said cannula;
   means to releasably retain said cannula at the distal end of said cylinder, said retaining means including a pair of movable jaws that are aligned with one another to engage said cannula therebetween; and
   means to move said jaws out of engagement with said cannula to permit said cannula to be removed from the distal end of said cylinder.

2. The syringe recited in claim 1, further comprising means for retracting said cannula into said cartridge at the interior of said cylinder after the contents of said cartridge have been injected and said jaws have been moved out of engagement with said cannula.

3. The syringe recited in claim 2, wherein the means for retracting said cannula is a piston which is movable axially through said cartridge, said piston movable through said cartridge for expulsing the supply of fluid therefrom and for receiving a portion of said cannula therewithin, said piston movable proximally through said cartridge to retract said cannula therewithin after said jaws have been moved out of engagement with said cannula.

4. The syringe recited in claim 1, wherein said jaws include respective hinge means around which said jaws rotate when moving out of engagement with said cannula.

5. The syringe recited in claim 4, wherein said jaws have respective contact faces between which said cannula is engaged and adjacent surfaces through which respective channels are formed, said contact faces being rotated out of engagement with said cannula and said adjacent surfaces being rotated into face-to-face alignment with one another, such that said cannula is received within the channels of said adjacent faces when said jaws are rotated around said hinge means.

6. The syringe recited in claim 1, further comprising bridge means having a pair of arms extending outwardly from the distal end of said cylinder and a cross member extending across the distal end of said cylinder between said arms, said cross member having an aperture formed therethrough for receiving and supporting said cannula in coaxial alignment with said cylinder.

7. The syringe recited in claim 6, wherein said jaws are connected to respective arms of said bridge means.

8. The syringe recited in claim 7, wherein said jaws are connected to said arms by means of respective hinges around which said jaws rotate when moving out of engagement with said cannula.

9. The syringe recited in claim 1, wherein said cannula has an irregularly textured surface located between said pair of jaws for enhancing the engagement of said cannula by said jaws.

10. The syringe recited in claim 1, wherein said means to move said jaws out of engagement with said cannula is said cartridge, said syringe further comprising means for advancing said cartridge distally through said cylinder and into contact with said jaws.

11. The syringe recited in claim 10, wherein said means for advancing said cartridge includes a piston assembly having a piston movable axially through said cartridge and a piston stem connected to said piston for controlling the axial movement of said piston through said cartridge.

12. The syringe recited in claim 11, wherein said piston stem is detachably connected to said piston.

13. A syringe comprising:
a hollow cylinder having proximal and distal ends, said cylinder having a supply of fluid located therewithin;
a hypodermic needle extending outwardly from the distal end of said cylinder and communicating with the fluid supply therewithin so that said fluid supply may be injected into a targeted tissue via said needle;
means for engaging and releasably retaining said needle at the distal end of said cylinder, said retaining means including a pair of jaws that are aligned with one another to engage said needle therebetween;
hinge means around which said jaws may rotate so that said jaws can be moved out of engagement with said needle; and
means to rotate said jaws around said hinge means to permit said needle to be removed from the distal end of said cylinder.

14. The syringe recited in claim 13, wherein said jaws have respective faces between which said needle is engaged and adjacent beveled surfaces through which respective channels are formed, said contact faces being rotated out of engagement with said needle and said adjacent surfaces being rotated into face-to-face alignment with one another, such that said needle is received within the channels of said adjacent surfaces when said jaws are rotated around said hinge means.

15. The syringe recited in claim 13, further comprising bridge means having a pair of arms extending outwardly from the distal end of said cylinder and a cross member extending across the distal end of said cylinder between said arms, said cross member having an aperture formed therethrough for receiving and supporting said needle in coaxial alignment with said cylinder.

16. The syringe recited in claim 15, wherein said jaws are attached to respective arms of said bridge means at said hinge means.

* * * * *